United States Patent [19]
Seebach et al.

[11] 3,957,823
[45] May 18, 1976

[54] ELECTROPHILIC SUBSTITUTION OF NITROSAMINES

[75] Inventors: Dieter Seebach, Lich; Dieter Enders, Giessen, both of Germany

[73] Assignee: Badische Anilin- & Soda-Fabrik Aktiengesellschaft, Ludwigshafen (Rhine), Germany

[22] Filed: Apr. 12, 1973

[21] Appl. No.: 350,345

[30] Foreign Application Priority Data
Apr. 15, 1972  Germany............................ 2218366
Sept. 22, 1972  Germany............................ 2246564

[52] U.S. Cl. ..................... 260/340.5; 260/239 B; 260/268 N; 260/326.85; 260/348 R; 260/563 R; 260/570.5 CA; 260/570.6; 260/570.8 R; 260/570.9; 260/583 CC; 260/584 R; 260/293.72; 260/293.9; 260/293.51; 260/283 R

[51] Int. Cl.² ....................................... C07D 317/06
[58] Field of Search ....... 260/583 CC, 340.5, 570.6; 424/167

[56] References Cited
OTHER PUBLICATIONS
Chemical Abstracts, Vol. 60, (1964), p. 7906e.
Chemical Abstracts, Vol. 74, (1971), p. 53743d.
Chemical Abstracts, Vol. 77, (1972), p. 34611e.

Primary Examiner—V. D. Turner
Attorney, Agent, or Firm—Johnston, Keil, Thompson & Shurtleff

[57] ABSTRACT

The invention relates to a process for the electrophilic substitution of nitrosamines on the carbon atom in the α-position to the amino nitrogen by metallizing the nitrosamine of a secondary amine and then reacting it with an electrophilic reagent.

7 Claims, No Drawings

ELECTROPHILIC SUBSTITUTION OF NITROSAMINES

The invention relates to a process for the electrophilic substitution of nitrosamines on the carbon atom in the α-position to the amino nitrogen. The process comprises metallizing the nitrosamine of a secondary amine which bears at least one hydrogen atom in the α-position to the amino nitrogen and reacting the metallized compound with an electrophile.

The starting compounds are N-nitrosamines which may be prepared by conventional methods such as are described for example in the review by L. Fridman, F. M. Mukhametshin and S. S. Novikov, Usp. Khim. 40, 34 (1971). Hydrogen atoms in the α-position to the amino nitrogen are replaced by metal and the organometallic compound obtained may be further reacted with an electrophile.

The process of the invention may be illustrated with reference to the reaction of dimethylnitrosamine which may be metallized with lithium diisopropylamine to form an organolithium compound which is then reacted with benzaldehyde according to the following equations:

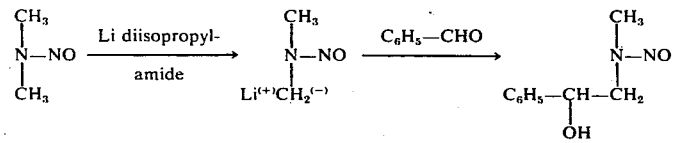

The fact that metallized nitrosamines (which have not so far been available) can be metallized is surprising. The metallized nitrosamines may be made utilizable for valuable syntheses by reaction with electrophiles. New syntheses are thus made available to industry by a process which is easy to carry out.

The only limitation on nitrosamines to be used for the reaction is that they should bear at least one hydrogen, replaceable by metal, in the α-position to the amino nitrogen so that they can be metallized in the α-position.

For the sake of simplicity some advantages nitrosamines are hereinafter identified by the secondary amines from which they are derived:

The simplest secondary aliphatic amine is dimethylamine. Other aliphatic amines, in each case with identical or different linear, branched or alicyclic substituents on the nitrogen atom, are similarly advantageous.

Suitable aliphatic radicals on the nitrogen atom include methyl, ethyl, propyl, butyl, isopropyl, tert.-butyl and amyl, and also long-chain radicals of up to twenty carbon atoms such as are usual in fatty amines. Particularly suitable alicyclic substituents are cycloalkyl radicals of five to seven ring carbon atoms.

The following secondary aliphatic amines are given as examples: methylethylamine, methyl-tert-butylamine, diethylamine, methylpropylamine, methylisopropylamine, diisopropylamine, methylhexylamine, methylstearylamine, methyloleylamine, methylcetylamine, methylcyclopentylamine, methylcyclohexylamine and methylcycloheptylamine.

The nitrosamines used may also be derived from cyclic secondary amines in which the nitrogen atom is a component of a ring preferably having from four to eight members and which may contain another heteroatom such as nitrogen or oxygen, e.g. aziridine, acetidine, pyrrolidine, piperidine, hexamethylenimine, heptamethylenimine, N-methylpiperazine and morpholine.

The alkyl radicals of the secondary amines may additionally bear groups which are not attacked in the metallization such as ether, acetal, thioacetal or dialkylamino groups. Nitrosamines which bear a cabonyl group in the β-position to the amino-nitrogen may also be subjected to reactions according to the invention.

Phenyl is a preferred substituent and methylbenzylamine and ethylbenzlamine are suitable secondary amines. The phenyl radical may bear halogen atoms such as fluoro and chloro, alkoxy, particularly methoxy, or dialkylamino, particularly dimethylamino.

A phenyl group may also be combined directly to the amino nitrogen so that aromatic amines such as methylaniline, ethylaniline or phenylbenzylamine may also be used.

The metal in the metallized nitrosamine compound may be an alkali metal such as lithium, sodium or potassium, an alkaline earth metal and particularly magnesium, or zinc, cadmium and copper as the monovalent copper cation. The preferred metals are the alkali metals and the preferred alkali metal is lithium.

Convenient metallizing reagents for replacing a hydrogen atom on the carbon atom in the α-position by the preferred metal include conventional organometallic compounds such as methyl lithium, tert.-butyl lithium, phenyl lithium, n-butyl lithium, lithium diisopropylamide, lithium dicyclohexylamide, lithium cyclohexylisopropylamide and the corresponding sodium and potassium compounds. Alkali metal hydrides such as sodium hydride or lithium hydride may also be used.

The magnesium compounds are advantageously prepared by means of alkyl or aryl magnesium halides such as phenyl magnesium bromide or methyl hagnesium chloride. Magnesium and particularly zinc, cadmium and copper may also be introduced by metal exchange reactions with alkali metals.

Because of the great reactivity and instability of metallized nitrosamines, it is advisable to carry out the metallization and also the further reactions with electrophiles at temperatures of from room temperature down to the low temperatures of liquid nitrogen. The reactions may be carried out advantageously at temperatures of from about −50° to −150°C.

Convenient solvents to be used for the metallization and the further reactions include inert aprotic solvents such as saturated aliphatic and cycloaliphatic hydrocarbons, e.g. pentane, isopentane, hexane and cyclohexane, if desired as mixtures, ethers for example diethyl ether, tetrahydrofuran, α-methyltetrahydrofuran, dioxane, dimethoxyethane, dimethoxymethane, dimethyl sulfoxide, and tertiary amines such as trimethylamine, tetramethylethylenediamine or diazabicyclooctane, if desired mixed with hydrocarbons.

Metallization of the nitrosamines is generally carried out by adding a solution of the metallizing agent to a solution of the nitrosamine. The converse procedure of adding the nitrosamine to the metallizing agent may also be used. The product is then reacted with the electrophile. In some cases as further described below the metallization of the nitrosamine is carried out in the presence of the electrophile. A preferred solvent is tetrahydrofuran containing the triamide of hexamethylphosphoric acid in which the stability of the metallized nitrosamines in considerably increased. The speed of the metallization may be increased by an addition of $LiClO_4$ to the tetrahydrofuran solution in a 1 to 5 molar excess based on the nitrosamine.

The metallized nitrosamines have an unexpectedly high reactivity with electrophiles.

Any conventional carbonelectrophilic compounds may be used as electrophiles. Electrophilic reagents also referred to in the literature as electrophiles, are described for example in C. K. Ingold, "Structure and Mechanism in Organic Chemistry", Ithaka, 1953, pages 211 et seq., or J. D. Roberts and M. Caserion, "Basic Principles of Organic Chemistry", New York 1964, pages 288 et seq. Their reactivity with carbonyl compounds is particularly noteworthy.

For example aldehydes or ketones of up to twenty carbon atoms may be reacted without limitation from among the carbonyl compounds. The yields are very high, in some cases more than 90 and 95%.

The following aldehydes and ketones are suitable: aliphatic aldehydes such as acetaldehyde, propionaldehyde, butyraldehyde, heptanal or pentadecanal, and aromatic aldehydes such as benzaldehyde, anisaldehyde, piperonal, and β-naphthaldehyde and also aliphatic, cycloaliphatic and aromatic ketones, for example acetone, methyl ethyl ketone, methyl isopropyl ketone, dipropyl ketone, dibutyl ketone, cyclopentanone, cyclohexanone, cycloheptanone, cyclooctanone, acetophenone and benzophenone.

Unsaturated carbonyl compounds such as acrolein, dimethylacrolein, mesityl oxide, cinnamaldehyde and 2-cyclohexen-1-one may also be used. Surprisingly the unsaturated carbonyl compounds do not enter into any Michael additions under the reaction conditions.

Halomethyl ketones such as chloroacetone or phenacyl bromide may also be reacted without difficulty. It is interesting that halomethyl ketones first react with the electrophilic carbonyl groups and then, depending on the conditions, an epoxide may be formed by elimination of hydrogen halide. At low temperatures the halohydrins are first formed whereas at higher temperatures, for example at room temperature the formation of epoxides takes place as may be seen from the reaction of lithium dimethyl nitrosamine with chloroacetone illustrated by the following equations:

agents include chloromethyl ethers or allyl halides, particularly allyl chloride, or sulfonic acid esters such as dimethyl sulfate, diethyl sulfate, methyl benzenesulfonate and esters of higher alcohols such as decyl benzenesulfonate or the equivalent tosyl esters.

Metallized nitrosopiperidine is for example alkylated by n-hexadecyl bromide in a yield of more than 50%.

Known acylating agents such as carboxylic acid chlorides, anhydrides, esters, amides, nitriles and isocyanates are also suitable as electrophiles. Preferred acylating agents are caboxylic acid derivatives of up to twenty carbon atoms in the carboxylic acid on which the compound is based.

Examples of these are: carbon dioxide, benzoyl chloride, chloroformic esters, acetyl chloride, ketene, formic esters, cabonic esters, acetic esters, butyric esters and esters of monohydric alcohols with fatty acids of up to twenty carbon atoms. Examples of esters of unsaturated carboxylic acids are ethyl acrylate, ethyl methacrylate, methyl crotonate and ethyl cinnamate. Alkali metal salts, particularly lithium salts, of carboxylic acids may also be used as acylating agents. Examples of carboxylic amides and nitriles are N,N-disubstituted amides of aliphatic or aromatic carboxylic acids such as dimethylformaide, N-formylpyrrolidine, N-formylpiperidine, N-formylmorpholine, dimethyl acetamide, dimethylbenzamide and aliphatic or aromatic caboxylic acid nitriles which may contain an olefinic double bond in the molecule, such as acetonitrile, propionitrile, adiponitrile, benzonitrile, acrylonitrile, methacrylonitrile or cinnamonitrile.

Isocyanates R-NCO which can be converted into the corresponding amide derivatives may also be used as electrophiles. Convenient isocyanates are those in which R is linear or branched alkyl of one to ten carbon atoms, aralkyl such as benzyl or phenylethyl, cycloalkyl of three to eight carbon atoms in the ring or aryl, preferably phenyl or naphthyl. The aromatic radicals may bear lower alkyl, such as methyl or ethyl, alkoxy, particularly methoxy or ethoxy, or halogen atoms such as fluorine or chlorine, as substituents.

It is of interest that by reaction with acid chlorides compounds may be formed which are regarded as diadducts of the metallized nitrosamine to the acid chloride. The reaction may be directed so that the 1:1 adduct (an α-acylnitrosamine) or the 2:1 adduct (a dinitroso-1,2-diaminopropanol-2) is formed:

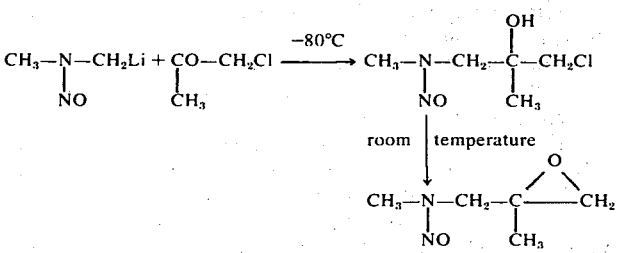

An alkylating agent, particularly an alkyl halide of up to twenty cabon atoms, may be used instead of a carbonyl compound as the electrophile. The following alkyl halides are suitable: primary iodides or bromides, for example methyl iodide, butyl iodide and also benzyl bromide or benzyl chloride. Other suitable alkylating

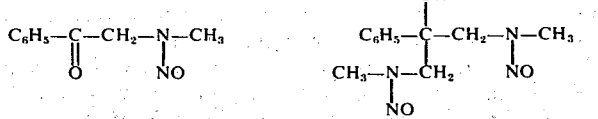

Not only carbon electrophiles, but also non-carbon or hetero electrophiles may be reacted with metallized nitrosoamines with advantage.

Examples of suitable non-carbon electrophiles are the elementary halogens $Cl_2$, $Br_2$ or $I_2$, halosilanes such as trimethylchlorosilane and dichlorodimethylsilane, the corresponding phenylsilanes and germanium compounds. Disulfides such as dialkyl disulfides, diaryl disulfides, dimethyl disulfide, diphenyl disulfide, sulfenyl chlorides and sulfonyl chlorides are examples of electrophilic sulfur compounds.

Oxygen and peroxides and also halophosphines, for example diphenyl chlorophosphine, and chloramines such as dimethylchloramine may also be used.

An example is the reaction of lithium dimethylnitrosamine with the non-carbon electrophile $I_2$ where a carbon-carbon union takes place resulting in a dimeric nitrosamine of the formula:

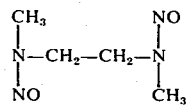

Reaction with the electrophile is generally carried out by adding the electrophile in pure or dissolved form if it is a liquid or in dissolved form, conveniently in one of the said solvents, if it is a solid, in the temperature range given above. The whole is allowed to stand for some time, if necessary up to twenty-four hours, to complete the reaction. The product is worked up as a rule by adding an equimolar amount of acetic acid at about −50°C and then pouring it into saturated common salt solution so that the nitrosamine formed can be recovered from the organic phase.

Alternatively a solution of nitrosamine with the electrophile (which if desired may serve in a large excess as the solvent) may be placed in a vessel and the metallizing agent added. In the case of metallization in the presence of the electrophile (which naturally should not react with the metallizing agent) the whole reaction may be carried out within the temperature range specified above, preferably in the upper temperature range up to room temperature.

It should be stressed that in the case of nitrosamines in which both primary and secondary hydrogen atoms in the α-position to the amino nitrogen can be replaced by metal it is possible surprisingly to control the end products.

It will be seen from Table II that in the reaction of metallized benzylmethylnitrosamine with acetaldehyde the ratio of the products a:b is 3:2 if the aldehyde is added three minutes after the metallization, whereas addition of the carbonyl compound one hour after the metallization results in a ratio of 1:2.

The Examples of Table II show that even nitrosamines having radicals with strong steric hindrance, as for example two isopropyl radicals, may be used. Other examples of radicals with strong steric hindrance will also be found in Table III.

Nitrosamines of cyclic secondary amines such as N-nitrosopiperidine or N-nitrosohexamethylenimine may be converted with particularly high yields of end products having asymmetric carbon atoms or diastereoisomerism. Acetaldehyde, propionaldehyde, benzaldehyde, benzophenone, propyl iodine and benzyl bromide are preferred from among the said electrophiles for this purpose.

Piperonal is for example stressed as an electrophile for the reaction with nitrosamines. Reactions with piperonal provide a new method for obtaining compounds of the series of catecholamines. Metallized tert-butylmethylnitrosamine also reacts with carbonyl compounds with high yields. The reaction of metallized nitrosamines with d,1-camphor is also emphasized.

As shown by the reaction of dimethylnitrosamine with benzaldehyde, the use of an asymmetric solvent such as diacetoxybutanediamine results in asymmetric induction.

The nitrosamines prepared by the process of the invention may be used for the elucidation of biochemical process. The nitrosamine compounds are also intermediates for chemical syntheses. They may be reduced by conventional methods, preferably by electrochemical methods, to unsymmetrically substituted hydrazines. Amino compounds which are accessible only with great difficulty by other methods may be obtained by denitrosation reactions. For example β-aminoalcohols are obtained after denitrosation from the reaction products with carbonyl compounds, and β-γ-epoxides of secondary amines from the reaction products with chloromethyl ketones, or with alkyl halides new radicals may be introduced into the carbon atom in the α-position to the amino nitrogen.

The reaction products of metallized nitrosamines with carbonyl compounds may be dehydrated as shown by the following equation:

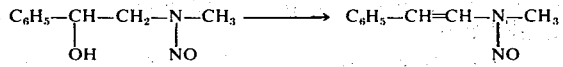

In this way new types of vinylnitrosamines may be prepared. The styrylmethylnitrosamine represented by the formula is obtained in a yield of more than 95% and has a melting point of 68°C.

The following Examples illustrate the invention.

EXAMPLE 1

I N-nitroso-N-methyl-1-hydroxy-2-aminophenylethane from dimethylnitrosamine and benzaldehyde:

a. Production of a solution of lithium diisopropylamide as metallizing agent:

7.26 ml of a 1.58 M solution of n-butyl lithium in n-hexane is added to a solution of 1.6 ml (1.15 g = 11.5 millimoles) of diisopropylamine in 30 ml of absolute tetrahydrofuran which is being stirred at −78°C under an excess pressure of 100 mm of argon or nitrogen. The temperature is allowed to rise to 0°C and the whole is cooled again to −78°C.

b. Production of lithium dimethylnitrosamine: A solution is prepared from 0.814 ml (0.82 g = 11.0 millimoles) of pure dimethylnitrosamine and 20 ml of absolute tetrahydrofuran while excluding air and the solution is stirred at −80°C. The whole of the solution prepared under (a) is added at once to the solution prepared under (b), the mixture being orange yellow in color.

c. Reaction with benzaldehyde: Ten minutes after the addition of lithium diisopropylamide has been completed 1.01 ml (1.06 g = 10.0 millimoles) of pure benzaldehyde is allowed to drip in at −80°C within two minutes, the color of the solution becoming lighter toward yellow. The whole is stirred for another hour at −80°C, the temperature is allowed to rise to −20°C, 1.30 ml (1.37 g = 22.6 millimoles) of acetic acid is added, the whole is poured into a mixture of 50 ml of methylene dichloride and 50 ml of saturated sodium chloride solution, the layers are separated and the aqueous phase is extracted twice, each time with 20 ml of the same solvent. The combined organic phase are washed once with saturated NaCl solution, dried over sodium sulfate and concentrated in a rotational evaporator. 2.10 g of a yellow oil remains and crystallizes. The crystals are freed from adherent volatile impurities in the vacuum of an oil pump. The yield is 1.76 g (98%) and the melting point is 73°C.

The crude oil may also be distilled in vacuo. Boiling point 160°C at 1 mm. Infrared spectrum of an oily sample (without solvent) in $cm^{-1}$; 3400 (OH), 3030 and 3060 (aromatic CH), 2930 (aliphatic CH), 1450 (NO), 1330 (C-N), 1060 (N-N), other intense bands at 1170, 760, 730 and 700. The complicated NMR sprectrum consists of two spectra of E- and Z-form; all bands and couplings can be assigned. II Variants of the method of Example 1:

a. Instead of adding the solution of lithium diiisopropylamide to that of the nitrosamine, the pure nitrosamine is added to the solution of lithium diiisopropylamide. In this way concentrated solutions of the metallized nitrosamine may be prepared from which a precipitate sometimes separates but passes into solution again when the electrophile is added.

b. Solutions of the lithium amides of cyclohexylisopropylamine and dicyclohexylamine and methyl, phenyl and tert-butyl lithium in ether, ether/benzene or n-hexane are used instead of the solution of lithium diiisopropylamide.

c. Absolute ether is used instead of tetrahydrofuran according to II(a).

EXAMPLE 2

III Production of N-nitroso-N-phenyl-2-hydroxy-1-aminopropane from phenylmethylnitrosamine and acetaldehyde:

7.26 ml (11.5 millimoles) of a 1.58 M solution of n-butyl lithium in n-hexane is added at 80°C under an inert gas to a solution of 1.62 g (11.5 millimoles) of isopropylcyclohexylamine in 35 ml of tetrahydrofuran. The whole is allowed to warm up to 0°C, 10 ml of absolute ether and 5 ml of petroleum ether (40/60) are added, the whole is cooled with a bath of pentane and liquid nitrogen to −120°C and a solution of 1.43 g of phenylmethylnitrosamine in 5 ml of tetrahydrofurane is added within two minutes with vigorous mixing in a turbomixer. A cloudy solution having an orange brown color is formed and after five minutes a 50% solution of 0.44 g of acetaldehyde (10 millimoles) in tetrahydrofuran is added. The reaction mixture becomes paler, is stirred for another two hours at below −100°C, warmed to −60° C and 0.7 ml of acetic acid (12 millimoles) in 5 ml of tetrahydrofuran is added. The whole is poured into a mixture of 30 ml of water, 1.1 g of concentrated hydrochloric acid and 30 ml of methylene chloride, shaken and the phases are separated. The aqueous phase is extracted again with methylene chloride and the combined methylene chloride solutions are dried over sodium sulfate and concentrated in a rotational evaporator. The oily residue is distilled in vacuo (100°C oilbath/$10^{-3}$ mm, microdistillation). The yield: NMR-spectroscopic in the crude product: 60%, after distillation (in which partial decomposition takes place) 0.54 g (30%), infrared spectrum (film): 3400 (OH), 3060 (aromatic CH), 2980–2870 (aliphatic CH), 1595 and 1495 (phenyl bands), other intense bands at 1470, 1440, 1090, 1030, 760, 690 $cm^{-1}$. The NMR spectrum exhibits the expected signals.

In the following Table further substituted nitrosamines are shown as Examples. In each case 10 millimoles of metallized nitrosamine is reacted with 10 millimoles of electrophile. The boiling points are bath temperature in the distillation with the molecular distillation apparatus. The columns in Table I are: A = nitrosamine; B = electrophile; C = method and metallizing agent; D = reaction period in hours of the Li-nitrosamine with electrophile; E = product; F = % yield of crude product (spectroscopic); G = % yield, distilled or recrystallized; H = boiling point/mm or melting point °C.

Table I

| A | B | C | D | E | F | G | H |
|---|---|---|---|---|---|---|---|
| Dimethylnitrosamine<br><br>$CH_3-N-CH_3$<br>$\|$<br>NO | Benzaldehyde | I. Diisopropylamide | 1 | $CH_3\!\!-\!\!N\!\!-\!\!CH_2\!\!-\!\!CH\!\!-\!\!C_6H_5$<br>ON $\quad$ OH | 100 | 90 | 73 |
| | | II a. Diisopropylamide | 1 | | 100 | 90 | |
| | | II b. $C_6H_5Li$ | 1 | | 80 | 70 | |
| | | IIb, $CH_3Li$ | 0.5 | | 70 | | |
| | | II c. Diisopropylamide | 1 | | 70 | 60 | |
| | n-butanol | I. Diisopropylamide | 2 | $CH_3\!\!-\!\!N\!\!-\!\!CH_2\!\!-\!\!CH\!\!-\!\!C_3H_7$<br>ON $\quad$ OH | 89 | 80 | 120/1 |
| | Acetone | II a. Diisopropylamide | 3 | $CH_3\!\!-\!\!N\!\!-\!\!CH_2\!\!-\!\!C(CH_3)\!\!-\!\!CH_3$<br>NO $\quad$ OH | 70 | 65 | 83/0.3 |
| | Benzophenone | I. Diisopropylamide | 3 | $CH_3\!\!-\!\!N\!\!-\!\!CH_2\!\!-\!\!C(C_6H_5)\!\!-\!\!C_6H_5$<br>NO $\quad$ OH | 75 | 70 | 113.5 |
| | Cyclohexanone | I. Diisopropylamide | 4 | $CH_3\text{-N-CH}_2\text{-cyclohexyl-OH}$<br>NO | 95 | 90 | 63(140/0.2) |
| | 2-Cyclohexen-1-one | I. Diisopropylamide | 3 | $CH_3\text{-N-CH}_2\text{-cyclohexenyl-OH}$<br>NO | 75 | 60 | 140/0.5 |
| | | II a. Diisopropylamide | 3 | | 85 | 75 | |

Table I-continued

| A | B | C | D | E | F | G | H |
|---|---|---|---|---|---|---|---|
| | Chloroacetone | IIa. Diisopropylamide | 15 −78° | $CH_3-N-CH_2-\underset{OH}{\overset{CH_3}{\underset{|}{C}}}-CH_2Cl$, N−NO | 90 | 85 | 90/10$^{-3}$ |
| | Chloroacetone | IIa. Diisopropylamide | 2 −78°; 20 −20 | $CH_3-N(NO)-CH_2-\underset{CH_3}{\overset{O}{\underset{\triangle}{C}}}-CH_2$ (epoxide) | 85 | 80 | 80/3 |
| | Phenacylbromide | II a. Diisopropylamide | 5 | $CH_3-N(NO)-CH_2-\underset{C_6H_5}{\overset{O}{\underset{\triangle}{C}}}-CH_2$ | 85 | 80 | 120/10$^{-3}$ |
| | Benzoylchloride (½ mole/mole amine) | I. Diisopropylamide | 3 | $CH_3-N(NO)-CH$ / $CH_3-N(NO)-CH_2$ bridged by C with $C_6H_5$ and OH | | 70 | 110 |
| | Methyliodide | I. Diisopropylamide | 4 | $CH_3-N(NO)-CH_2-CH_3$ | 80 | 75 | 80/30 |
| | n-Butyliodide | I. Diisopropylamide | 2 | $CH_3-N(NO)-CH_2-C_4H_9$ | 80 | 75 | 100/10 |
| | Benzylbromide | I. Diisopropylamide | 2 | $CH_3-N(NO)-CH_2-CH_2-C_6H_5$ | >95 | 95 | 100/0.1 |
| | iodine (½ mole iodine per mole nitrosamine) | I. Diisopropylamide | 0.5 | $CH_3-N(NO)-CH_2-CH_2-N(NO)-CH_3$ | >95 | 95 | 57 |
| Methylethyl nitrosamine $CH_3-CH_2-N(NO)-CH_3$ | Acetaldehyde | II a. Diisopropylamide | 2 | $CH_3CH_2-N(NO)-CH_2-CH(OH)-CH_3$ | 75 | 60 | 80 0.1 |
| Methylisopropyl-nitrosamine $(CH_3)_2CH-N(NO)-CH_3$ | Acetaldehyde | II a. Diisopropylamide | 5.5 | $(CH_3)_2CH-N(NO)-CH_2-CH(OH)-CH_3$ | 85 | 77 | 85/0.01 |
| Di-n-hexylnitrosamine n-$C_6H_{13}$−N(NO)−n-$C_6H_{13}$ | Benzylbromide | II a. Diisopropylamide | 8 | n-$C_6H_{13}$−N(NOCH$_2$−C$_6$H$_5$)−CH−C$_5$H$_{11}$ | 90 | | undistillable oil |
| N-Nitroso-pyrrolidine | Benzylbromide | II a. Diisopropylamide | 4 | pyrrolidinyl-N(NO)-CH$_2$C$_6$H$_5$ | 95 | 75 | 130/10$^{-3}$ |
| | carbon dioxide | II a. Diisopropylamide | Solution of Li compound poured on CO$_2$ | pyrrolidinyl-N(NO)-COOH | | 10 | 95° decomposes |
| N-Nitroso N-methyl-piperazine | Acetaldehyde | II a. Diisopropylamide | 9 | N-methyl-piperazine with NO and CH(OH)-CH$_3$ | 60 | 30 | 100/10$^{-3}$ |
| Phenylmethylnitros-amine $C_6H_5-N(NO)-CH_3$ | Acetaldehyde | III. Cyclohexyl-diisopropylamide | 2 | $C_6H_5-N(NO)-CH_2-CH(OH)-CH_3$ | 60 | 30 | 100/10$^{-3}$ |
| | | III. Dicyclohexylamide | 2 | | 45 | | |

TABLE II

| Nitrosamine | Electrophile | Product | Yield% | bp/mmHg or mp °C |
|---|---|---|---|---|
| Benzylmethyl-nitrosamine $C_6H_5-CH_2-N(NO)-CH_3$ | Acetaldehyde | (a) $C_6H_5-CH_2-N(NO)-CH_2-CH(OH)-CH_3$ | 95 | 120–130/0.01 |

TABLE II-continued

| Nitrosamine | Electrophile | Product | Yield% | bp/mmHg or mp °C |
|---|---|---|---|---|
| | | (b) $C_6H_5-CH-N-CH_3$ <br> $\phantom{xxxx}CH_3-CH-NO$ <br> $\phantom{xxxxxxxxx}OH$ | (a:b = 3:2 <br> a:b = 1:2) | |
| Diisopropyl-nitrosamine <br> $CH_3$ <br> $\phantom{xx}\diagdown$ <br> $\phantom{xxx}CH-N-CH$ <br> $CH_3\phantom{xxx}\vert\phantom{xxx}CH_3$ <br> $\phantom{xxxxxx}NO\phantom{xx}CH_3$ | Acetaldehyde | $CH_3\phantom{xx}CH_3\phantom{x}CH_3$ <br> $\phantom{xxx}\diagdown\phantom{xxx}\diagup$ <br> $\phantom{xxxx}CH-N-C-C$ <br> $CH_3\phantom{xxxx}\vert\phantom{x}\vert\phantom{x}\diagdown H$ <br> $\phantom{xxxxxx}NO\phantom{x}OH$ | 35 | 46.5–47 <br> (95/0.01) |
| N-nitroso-piperidine <br> ⌬ <br> N <br> NO | Benzylbromide | ⌬-$CH_2-C_6H_5$ <br> N <br> NO | 65 | 150/0.01 |
| | Acetaldehyde | ⌬ H H <br> N-C-$CH_3$ <br> NO OH <br> diastereoisomers | 90 | 100/0.001 |
| tert.-butyl-methyl-nitrosamine <br> $\phantom{xx}CH_3$ <br> $CH_3-C-N-CH_3$ <br> $\phantom{xx}CH_3\phantom{x}NO$ | Acetaldehyde | $CH_3$ <br> $CH_3-C-N-CH_2-CH-CH_3$ <br> $\phantom{xx}\vert\phantom{xxx}\vert\phantom{xxxxxx}\vert$ <br> $\phantom{xx}CH_3\phantom{x}NO\phantom{xxxx}OH$ | 90 | 70/0.03 |
| | Piperonal | $CH_2$⟨O⟩-benzene-$C(OH)-CH-N(NOCH_3)-C(CH_3)_3$ | 80 | 84 |
| Isopropylmethylnitrosamine <br> $CH_3$ <br> $\phantom{xx}\diagdown$ <br> $\phantom{xxx}CH-N-CH_3$ <br> $CH_3\phantom{xxxx}\vert$ <br> $\phantom{xxxxxxx}NO$ | Benzylbromide | $CH_3$ <br> $\phantom{xx}\diagdown$ <br> $\phantom{xxx}CH-N-CH_2-CH_2-C_6H_5$ <br> $CH_3\phantom{xxxx}\vert$ <br> $\phantom{xxxxxxx}NO$ | 90 | |
| N-Nitroso-hexamethyleneamine <br> ⌬ <br> N <br> NO | Benzophenone | ⌬ $C_6H_5$ <br> N-C-$C_6H_5$ <br> NO OH | 90 | 140 |
| Dimethylnitrosamine <br> $CH_3-N-CH_3$ <br> $\phantom{xxxx}\vert$ <br> $\phantom{xxxx}NO$ | Benzaldehyde (solvent: diacetoxybutanediamine) | $\phantom{xxxx}H$ <br> $CH_3-N-C-C_6H_5$ <br> $\phantom{xxxx}\vert\phantom{x}\vert$ <br> $\phantom{xxxx}NO\phantom{x}OH$ <br> $[\alpha]_D^{20} = -6°(c=1,CH_2Cl_2)$ <br> positive cotton effect = 356 nm | 75 | 74 <br> (to 95) |

The following method is a convenient one for the reactions set out in Table II:

33.0 millimoles of pure nitrosamine is added at about −78°C to 34.5 millimoles of lithium diiisopropylamide (prepared from diisopropylamine and butyl lithium) in 125 ml of a mixture of tetrahydrofuran and n-hexane in a ratio of 3:1. After the whole has stood for ten minutes 35.0 millimoles of electrophile is added. The mixture is kept for three hours at the temperature of dry ice (carbon dioxide snow), and is then allowed to warm up to a temperature of about 20°C. The end product is isolated in the usual way.

Amino compounds which are only accessible with great difficulty by other methods may be prepared from nitrosamines produced according to the invention by denitrosation reactions.

Denitrosation of the reaction product from metallized isopropylmethylnitrosamine with benzyl bromide will be described by way of example:

The reaction mixture formed as described above is heated to a temperature of about 20°C and freed from solvent. The residue is dissolved in 65 ml of glacial acetic acid containing 7% of hydrogen bromide. The whole is stirred for thirty minutes and the mixture is poured into aqueous caustic soda solution while cooling. The mixture is shaken with ether and β-phenylethylisopropylamine is precipitated from the ether as the hydrochloride by passing in gaseous hydrogen chloride.

The yield is 80% and the melting point is 162.5° to 165.5°C.

To avoid contact with the nitrosamines as much as possible in the reactions the following general procedure may be followed:

An equimolar mixture of pure secondary amine and pure alkyl nitrite (for example isoamyl nitrite) is stirred for five hours at 60°C and the alcohol formed is distilled off in vacuo from the residual nitrosamine. In the case of volatile amines with ethyl nitrite the reaction may be carried out in a solvent, for example tetrahydrofuran, at room temperature, the reaction period being about one day. It is not necessary to remove the alcohol formed if two equivalent of metallizing agent is added in the metallization which follows. Transfer of the nitroso groups may be carried out in the same flask as the subsequent reactions. The progress of the reaction may be followed by NMR-spectroscopy. After the reaction is over, the product may be dissolved in tetrahydrofuran and metallized in the usual manner.

EXAMPLE 3

Direct conversion of isopropylmethylamine into β-phenylethylisopropylamine in a single vessel:

1.47 g (20 millimoles) of isopropylmethylamine and 2.66 ml (2.34 g = 20 millimoles) isoamyl nitrite are mixed without solvent under nitrogen as an inert gas in a 100 ml flask having a lateral attachment. The flask is immersed for 5 hours in a bath heated to 60°C. After removal from the bath 60 ml of tetrahydrofuran is added and the solution formed is cooled to −78°C. 40 millimoles of lithium diiisopropylamide (in 20 ml of tetrahydrofuran and 27 ml of hexane) is added while stirring and ten minutes later 2.38 ml (20 millimoles) of benzyl bromide is added. After having been allowed to stand for 12 hours at −78°C the solvent is removed and the nitroso group eliminated with hydrogen bromide as described above. The yield of hydrochloride is 2.14 g (60%).

In the following Table III the formulae representing the reaction are followed by numbers of which the upper number is the yield % and the number beneath it is either the boiling point °C and the pressure in mm (e.g. 80/005) or the melting point in °C (e.g. 69.5). LDA is an abbreviation for lithium diisopropylamide.

TABLE III

| No. | Reaction | | | Yield / bp or mp |
|---|---|---|---|---|
| 1 | $(CH_3)_3C-N(NO)-CH_3$ | (1)LDA (2)$C_6H_5CH_2-Br$ | $(CH_3)_3C-N(NO)-CH_2-CH_2C_6H_5$ | more than 95 / 69.5 |
| 2 | $(CH_3)_3C-N(NO)-(CH_2)_2-C_6H_5$ | (1)LDA (2)$C_6H_5CH_2-Br$ | $(CH_3)_3C-N(NO)-CH(CH_2-C_6H_5)_2$ | 70 / 140 |
| 3 | cyclohexyl-N(NO)-CH$_3$ | (1)LDA (2)$(C_6H_5)_2CO$ | cyclohexyl-N(NO)-CH$_2$-CH(C$_6$H$_5$)$_2$(OH) | 95 / 117 |
| 4 | pyrrolidinyl-NO | | pyrrolidinyl(NO)-CH$_2$-CH$_2$-CH$_3$ | |
| 5 | piperidinyl-NO | (1)LDA (2)$CH_3-CH_2-CHO$ | piperidinyl(NO)-CH(OH)-CH$_2$-CH$_3$ Nitroso-conhydrin | 90 / oil |
| 6 | piperidinyl-NO | (1)LDA (2)$CH_3-CH_2-CH_2-I$ | piperidinyl(NO)-CH$_2$-CH$_2$-CH$_3$ Nitroso-coniin | 60 / 70/005 |
| 7 | menthyl-N(NO)-CH$_3$ | (1)LDA (2)$I_2$ | bis(menthyl-N(NO))-CH$_2$-CH$_2$ | more than 90 / oil |
| 8 | methylenedioxytetrahydroisoquinoline-N-NO | (1)LDA (2)$C_6H_5CH_2Br$ | methylenedioxytetrahydroisoquinoline(N-NO)-CH$_2$-C$_6$H$_5$ | (hydrochloride) 30 / 187–188 |
| 9 | $CH_3-N(NO)-CH_3$ | LDA d,l-camphor | camphor-CH$_2$-N(NO)-CH$_3$ (OH) | 68 / 104 |

TABLE III-continued

| No. | Reaction | | | |
|---|---|---|---|---|
| 10 | CH₃—N—CH₃<br>\|<br>NO | LDA<br>⟶<br>C₆H₅-COOCH₃ | C₆H₅—C—CH₂—N—CH₃<br>‖ \|<br>O NO | 35<br>115 |

It is also possible for example to carry out reactions of metallized n-decylmethylnitrosamine or octadecyl-tert.-butylnitrosamine with octanal, -naphthaldehyde, ketone, cyclohexanone, benzophenone, decyl iodide, palmityl chloride, acetone hydride and N,N-dimethylacetamide, the following compounds being obtained:

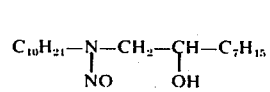
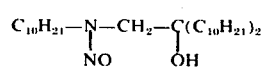
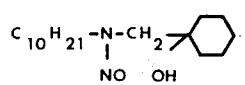
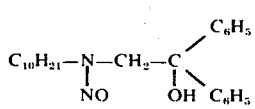

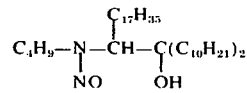
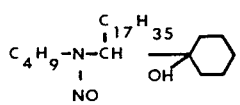
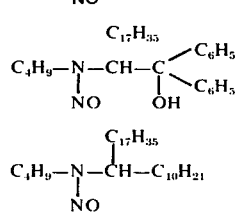

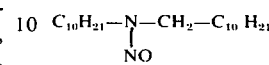
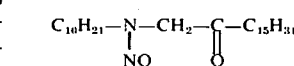
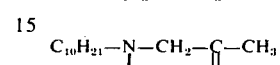
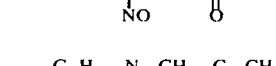
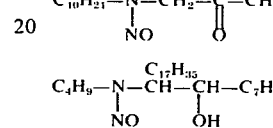
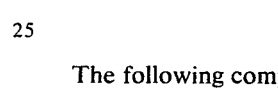
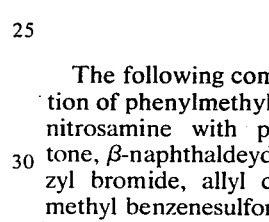

The following compounds are obtained by the reaction of phenylmethylnitrosamine or benzyl-tert.-butylnitrosamine with pentadecanal, methylisopropylketone, β-naphthaldeyde, cyclopentanone, acrolein, benzyl bromide, allyl chloride, methyl isovalerate and methyl benzenesulfonate:

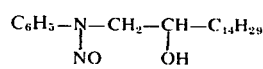
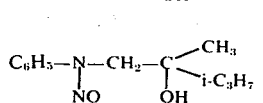
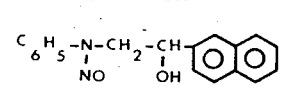
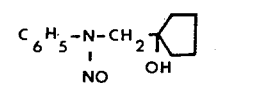
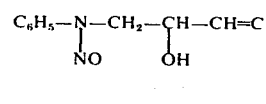
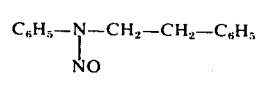
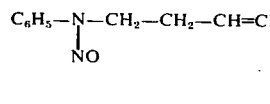
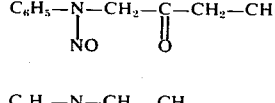
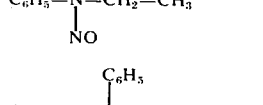
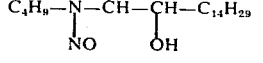

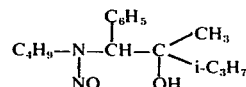
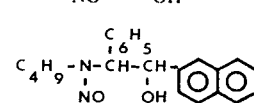
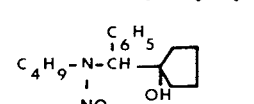
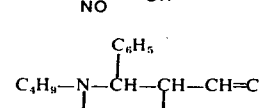
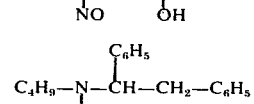
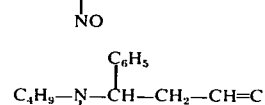
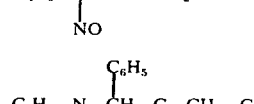
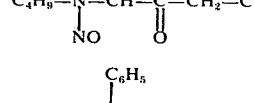
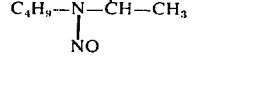

The following compounds are obtained by reaction of nitrosopyrrolidone or phenylethylnitrosoamine with 2-ethylhexanol, p-methoxybenzaldehyde, acetophenone, octadecyl bromide, methyl stearate and acetonitrile:

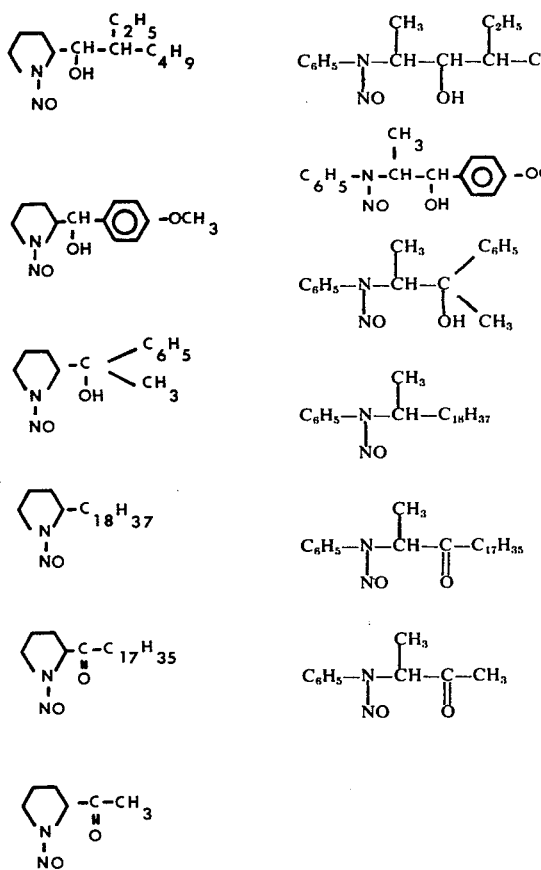

The following compounds are obtained by reaction of cyclohexylmethylnitrosamine with cyclohexen-2-one, mesityl oxide, 3,4-dimethoxycinnamaldehyde and ethyl acrylate:

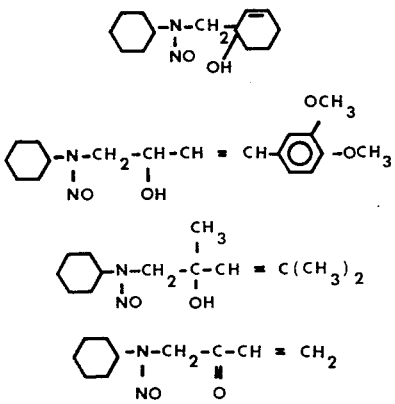

The following compounds are obtained by reaction of dimethylnitrosamine with p-dimethylaminobenzaldehyde, succinic anhydride, 1-iodo-3-chloropropane, phenylchloromethyl ether, decyl benzenesulfonate, ethyl crotonate, ethyl cinnamate, ethyl isocyanate, benzyl isocyanate, cyclohexyl isocyanate and phenyl isocyanate:

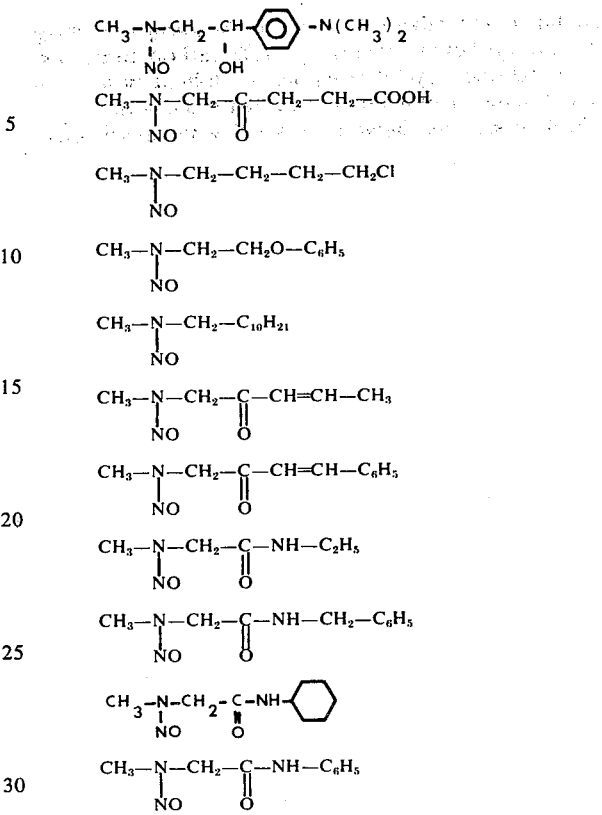

We claim:
1. A process for the electrophilic substitution of a nitrosamine of a secondary amine bearing at least one hydrogen atom in α-position to the amino nitrogen, said secondary amine having as its N-substituent alkyl having 1–20 carbon atoms, cyclopentyl, cyclohexyl, cycloheptyl, phenyl or benzyl, which comprises metallizing the α-hydrogen atom by reaction of said secondary amine with lithium, sodium or potassium diisopropylamide, in an inert aprotic solvent at a temperature of from room temperature down to the temperature of liquid nitrogen, and reacting the metallized nitrosamine at a temperature from room temperature down to the temperature of liquid nitrogen with an equimolecular amount of an electrophile selected from the group consisting of a saturated aliphatic aldehyde with up to twenty carbon atoms, benzaldehyde, anisaldehyde, piperonal, β-naphthaldehyde, a dialkyl ketone having up to 20 carbon atoms, cyclopentanone, cyclohexanone, cycloheptanone, cyclooctanone, acetophenone, benzophenone, acrolein, dimethylacrolein, mesityl oxide, cinnamaldehyde and 2-cyclohexen-1-one.

2. A process as claimed in claim 1 wherein the reactions are carried out at a temperature of from −50°C to −150°C.

3. A process as claimed in claim 1 wherein the reactions are carried out in tetrahydrofuran.

4. A process as claimed in claim 3 wherein $LiClO_4$ is added to the tetrahydrofuran in a 1 to 5 molar excess based on the nitrosamine.

5. A process as claimed in claim 1 wherein said electrophile is a saturated aliphatic aldehyde having up to 20 carbon atoms, benzaldehyde, anisaldehyde, piperonal or β-naththaldehyde.

6. A process as claimed in claim 1 wherein said electrophile is a member selected from the group consisting of a dialkyl ketone having up to 20 carbon atoms, cyclopentanone, cyclohexanone, cycloheptanone, cyclooctanone, acetophenone and benzophenone.

7. A process as claimed in claim 1 wherein said electrophile is an unsaturated carbonyl compound selected from the group consisting of acrolein, dimethylacrolein, mesityl oxide, cinnamaldehyde and 2-cyclohexen-1-one.

* * * * *

UNITED STATES PATENT AND TRADEMARK OFFICE
CERTIFICATE OF CORRECTION

PATENT NO. : 3,957,823
DATED : May 18, 1976
INVENTOR(S) : Dieter Seebach et al.

It is certified that error appears in the above-identified patent and that said Letters Patent are hereby corrected as shown below:

In Column 3, Line 64, delete " twenty cabon atoms,... " and substitute -- twenty carbon atoms,... --

In Columns 9 and 10, Table I, the 12th formula under the Heading "E" delete

"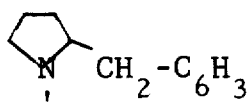"

and substitute

--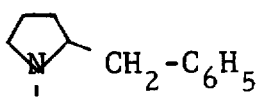--

In Columns 9 and 10, Table I, the 9th formula under the Heading "E", there should be a single bond between N and NO.

In Columns 9 and 10, Table II, the first formula under the Heading "Nitrosamine" there should be a single bond between N and NO.

In Columns 13 and 14, Table III, delete

" ⟶ 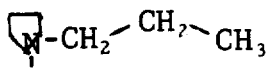"

UNITED STATES PATENT AND TRADEMARK OFFICE
CERTIFICATE OF CORRECTION

PATENT NO. : 3,957,823
DATED : May 18, 1976
INVENTOR(S) : Dieter Seebach et al.

It is certified that error appears in the above—identified patent and that said Letters Patent are hereby corrected as shown below:

and substitute

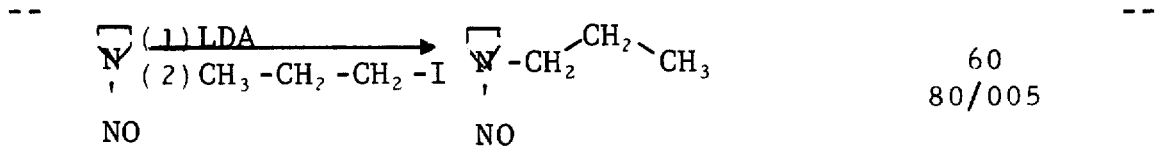

In Column 18, Lines 10-14, delete " $CH_3-\underset{NO}{N}-CH_2-CH_2O-C_6H_5$ "

and substitute -- $CH_3-\underset{NO}{N}-CH_2-CH_2-O-C_6H_5$ --

Signed and Sealed this

Twenty-sixth Day of April 1977

[SEAL]

Attest:

RUTH C. MASON
Attesting Officer

C. MARSHALL DANN
Commissioner of Patents and Trademarks